(12) United States Patent
Miller et al.

(10) Patent No.: US 6,470,895 B1
(45) Date of Patent: Oct. 29, 2002

(54) PEDICURE TOOL

(76) Inventors: Heidi M. Miller, 1101-D W. Melinda, Phoenix, AZ (US) 85027; Wayne A. Miller, 1101-D W. Melinda, Phoenix, AZ (US) 85027

( * ) Notice: Subject to any disclaimer, the term of this patent is extended or adjusted under 35 U.S.C. 154(b) by 0 days.

(21) Appl. No.: 09/896,280

(22) Filed: Jun. 29, 2001

(51) Int. Cl.⁷ .......................... A45D 29/18; A45D 29/04
(52) U.S. Cl. ..................... 132/76.4; 132/75.6; 132/76.5
(58) Field of Search .............................. 132/76.5, 76.4, 132/73.5, 75.6, 73

(56) References Cited

U.S. PATENT DOCUMENTS

| | | | | |
|---|---|---|---|---|
| 756,071 A | * | 3/1904 | Smith .......................... | 132/75.6 |
| 1,023,915 A | * | 4/1912 | Bates .......................... | 132/76.4 |
| 1,053,839 A | * | 2/1913 | Lomberg ..................... | 132/75.6 |
| 1,416,619 A | * | 5/1922 | Davis .......................... | 132/75.6 |
| 1,575,533 A | | 3/1926 | Brierley | |
| 1,643,164 A | | 9/1927 | MacDougall | |
| 2,091,807 A | * | 8/1937 | Crum .......................... | 132/75.6 |
| 2,376,946 A | * | 5/1945 | Stinson ....................... | 132/75.6 |
| 2,801,640 A | * | 8/1957 | Steele ......................... | 132/75.6 |
| 3,706,316 A | * | 12/1972 | Ishii ........................... | 132/76.4 |
| 4,184,499 A | * | 1/1980 | Seidler ....................... | 132/75.6 |
| 4,541,443 A | * | 9/1985 | Brothers et al. ........... | 132/75.6 |
| 4,757,571 A | | 7/1988 | Young | |
| 5,349,969 A | * | 9/1994 | Price .......................... | 132/76.5 |
| 5,899,210 A | | 5/1999 | Letherby et al. | |

* cited by examiner

Primary Examiner—John J. Wilson
Assistant Examiner—Robyn Kieu Doan
(74) Attorney, Agent, or Firm—Frank J. McGue

(57) ABSTRACT

A pedicure tool is disclosed which comprises a generally elliptical housing having at least three openings extending therethrough. Each of the at least three openings is adapted to releasably receive a concave insert panel therein. Further, each insert panel has an abrasive surface on the exterior thereof.

15 Claims, 4 Drawing Sheets

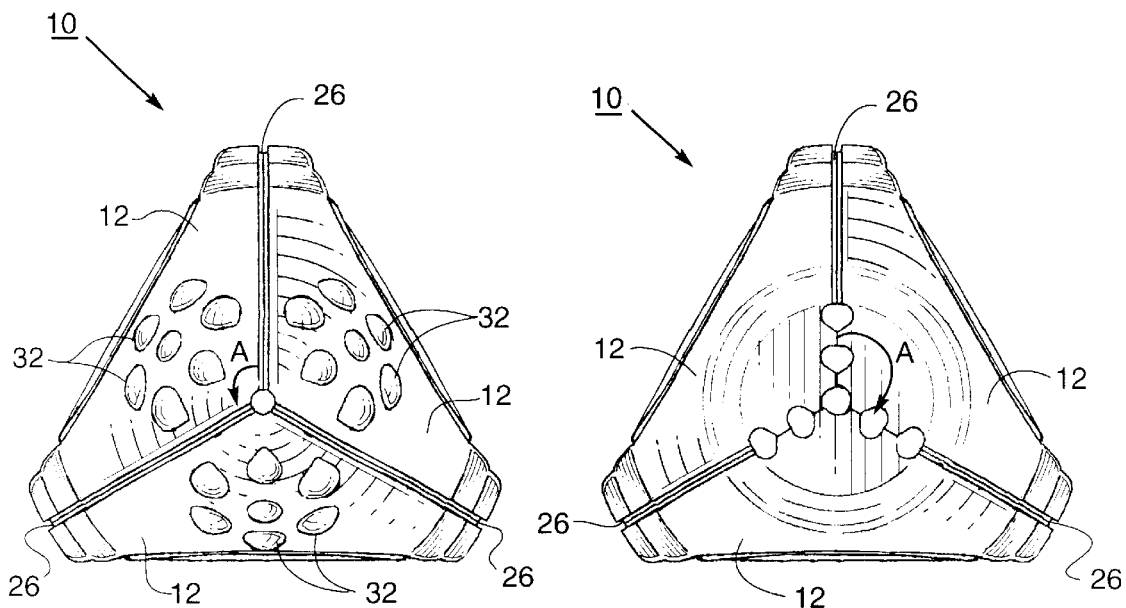
*FIG. 2.*    *FIG. 3.*
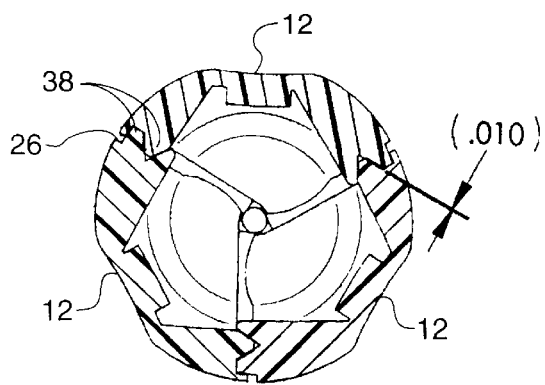
*FIG. 4.*

PEDICURE TOOL

TECHNICAL FIELD

This invention relates in general to pedicure tools, and, more particularly, to pedicure tools having replaceable sandpaper inserts.

BACKGROUND OF THE INVENTION

There are a number of pedicure tools on the market today. Such devices includes, in addition to nail clippers, rasps, files and massage tools for use on the feet. However, such rasps and files generally have only one grit fineness available though there are some two sided rasps present in the market. Thus, the ability to quickly switch from one grit fineness to another is limited. Further, it is desirable to provide the ability to quickly and easily change abrasive surfaces either between clients for sanitary reasons or when the abrasive surface is worn and needs changing.

U.S. Pat. No. 5,899,210 entitled "Nail Tool Having Multiples Surface" which issued on May 4, 1999 to Letherby et al. shows a nail tool having three planar surfaces having an abrasive thereon. However, Letherby et al. do not show a device whose abrasive surfaces can be changed quickly or easily.

Another desirable feature is the incorporation of a massage tool with the file or rasp tool. Further, the abrasive surface is preferably concave for functionality and ease of use.

None of the devices of the prior art meet this need.

SUMMARY OF THE INVENTION

It is an object of this invention to provide a pedicure tool adapted to provide three rasping concave surfaces thereon.

It is a further object of this invention to provide a pedicure tool having a massager integrated therewith.

Further objects and advantages of the invention will become apparent as the following description proceeds and the features of novelty which characterize this invention will be pointed out with particularity in the claims annexed to and forming a part of this specification.

BRIEF DESCRIPTION OF THE INVENTION

The present invention may be more readily described by reference to the accompanying drawings in which:

FIG. 2 is a top view of the embodiment of FIG. 1;

FIG. 3 is a bottom view of the embodiment of FIG. 1;

FIG. 4 is a cross sectional view of the embodiment of FIG. 1 taken along line 4—4;

DESCRIPTION OF THE PREFERRED EMBODIMENT

Figure 1:
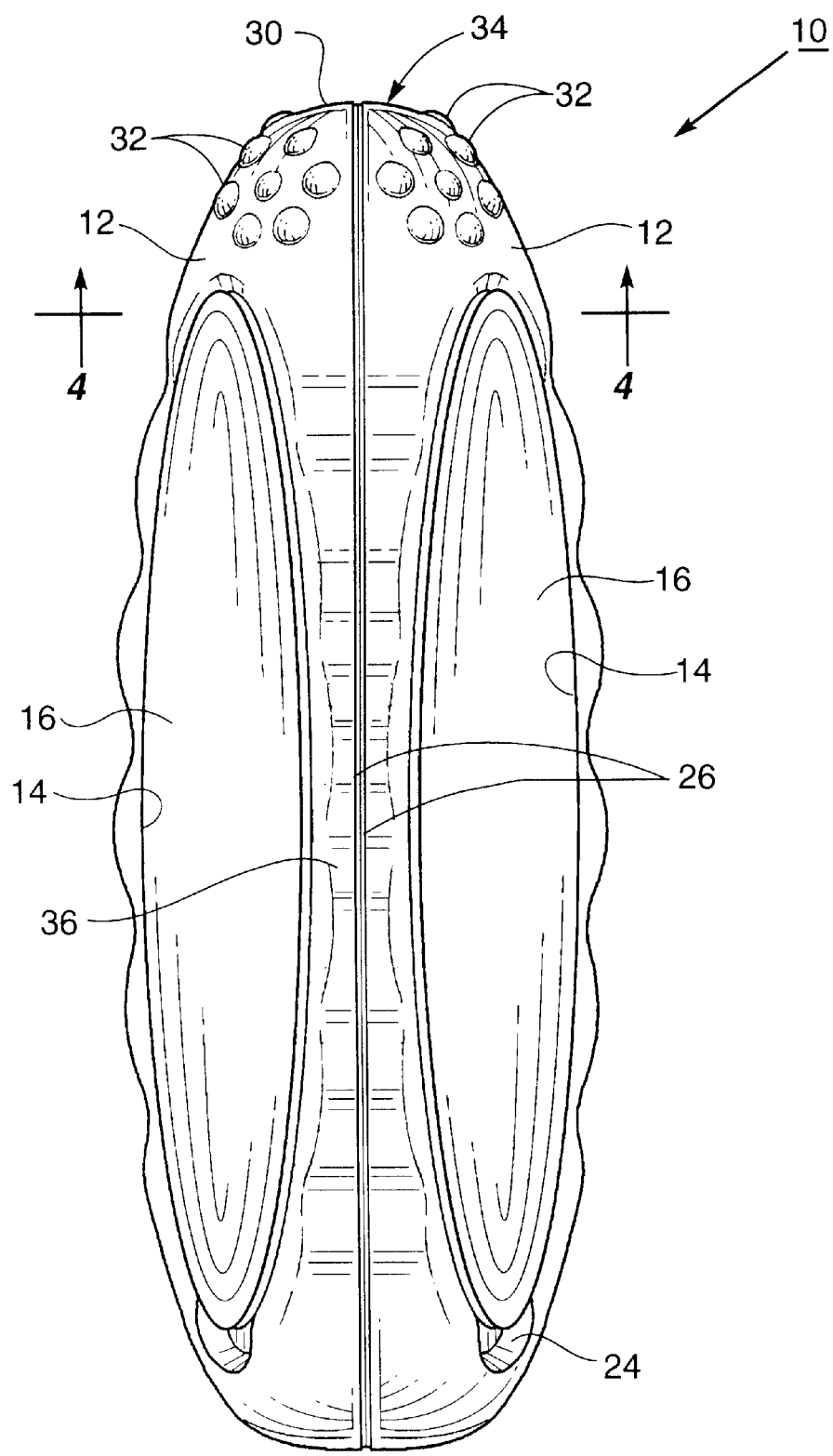
FIG. 1 is a perspective view showing the present invention.
Figure 5:
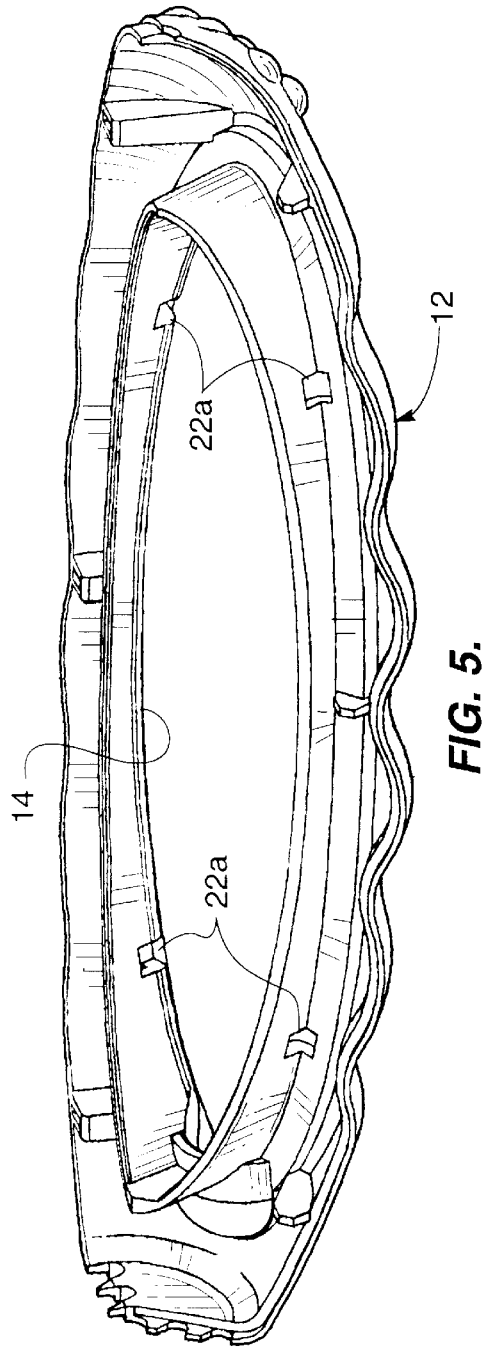
FIG. 5 is a perspective view showing a body panel of the present invention.

In the presently preferred embodiment shown in FIGS. 1–9, a pedicure device 10 of the present invention comprises three identical snap together body panels 12, each body panel 12 having an oval opening 14, each oval opening 14 adapted to receive an insert panel 16. Those skilled in the art will recognize that the use of three identical panels is preferred because of the economies of production. However, the present invention is not limited to the example described herein.

Figure 7:
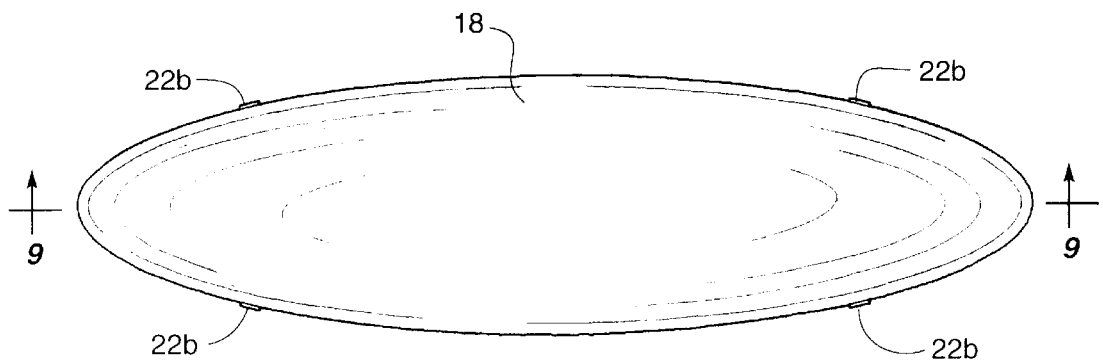
FIG. 7 is a top view of an insert panel of the present invention.
Figure 8:
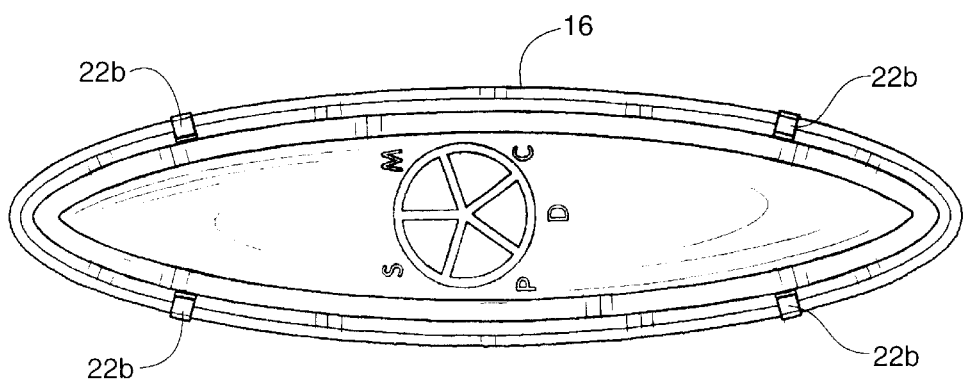
FIG. 8 is a bottom view of the insert panel of FIG. 6.
Figure 9:
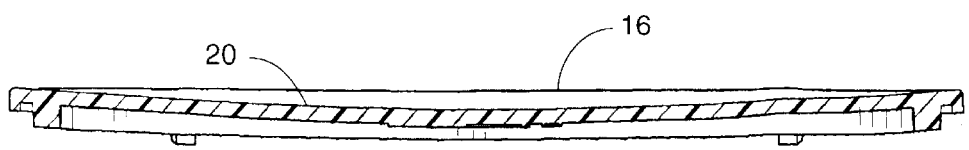
FIG. 9 is a cross sectional view of the insert panel of FIG. 6 taken along line 8—8.

In the illustrated embodiment, oval openings 14 and corresponding insert panels 16 are elongated outwardly concave oval shapes as best seen in FIGS. 7–9. Those skilled in the are will recognize that the principles of the invention are not limited to the particular shapes of the illustrated embodiment.

As best seen in FIG. 7, an exterior face 18 includes a grit 20 made of aluminum oxide or silicon carbide materials or any other material suitable for pedicure abrading applications. In the preferred embodiment, each concave insert panel 16 has one of three differing sandpaper grits, preferably classified as a fine, a medium and a coarse grit. The outwardly concave geometry of insert panel 16 is most preferred as it strongly enhances functionality and ease of use by easing access to exterior face 18.

Figure 6:
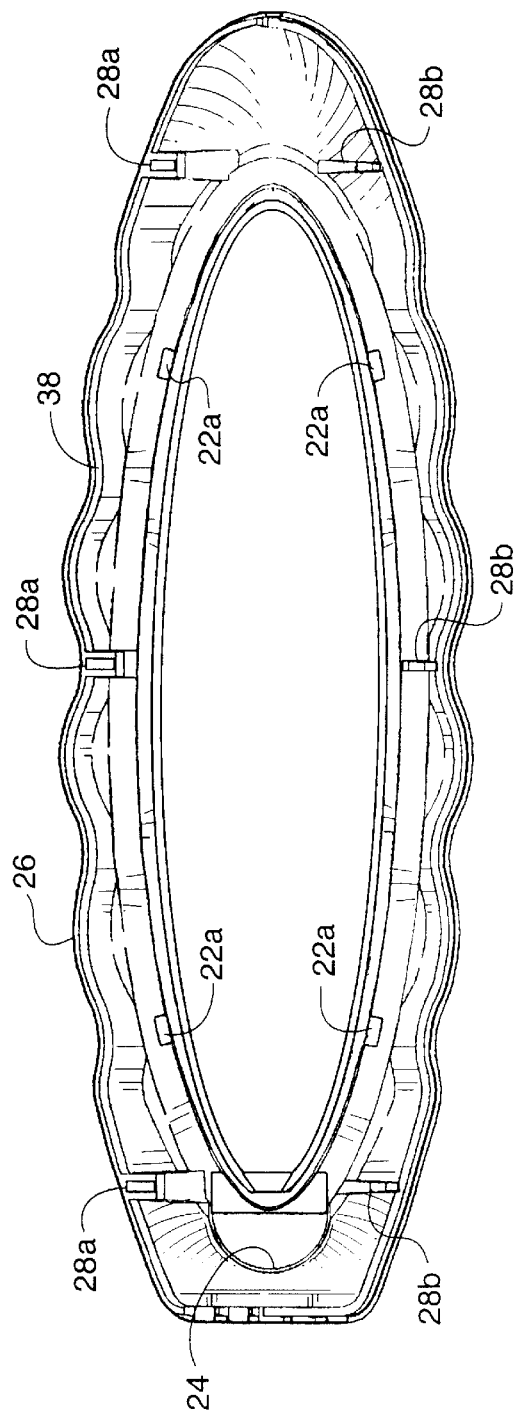
FIG. 6 is a bottom view of the body panel of FIG. 5.

As best seen in FIGS. 6 and 7, each insert panel 16 is detachably retained in oval opening 14. In the presently preferred embodiment, such retention is accomplished by body panel clip members 22a which abut corresponding oval opening 14 mating with corresponding insert panel clip members 22b positioned about the periphery of insert panel 16. A finger opening 24 is provided along one side of oval opening 14 which allows a user to engage insert panel 16 with a digit to easily remove same to replace, for example, worn sandpaper or for sanitary purposes.

Each body panel 12 forms a generally oval periphery 26 which mates with the corresponding a periphery of an abutting body panel 12. As best seen in FIGS. 2–4, when viewed from one end, peripheries 26 form an angle A which is one hundred twenty degrees (120°). Snap elements 28a along one side of body panel 12 mate with corresponding snap elements 28b on the opposite mating periphery 26 of an abutting body panel 12 to releasably hold the three body panels 12 together, forming, in combination, an ellipsoidal hollow housing 30. To provide additional structural integrity, as best seen in FIG. 4, peripheries 26 are further provided with interlocking teeth 38 when viewed in profile.

In the presently preferred embodiment, a plurality of massager bumps 32 are provided at one end of each body panel 12 to form, in combination, a massager tool 34 along one side of housing 30.

To use, an individual simply grasps the exterior of housing 30 to manipulate same. Alternatively, two of insert panels 16 can be removed whereby the portion of body panels 12 between the removed insert panels 16 form a handle 36 adapted to be grasped by a user as best seen in FIG. 1.

Although only certain embodiments have been illustrated and described, it will be apparent to those skilled in the art that various changes and modifications may be made therein without departing from the spirit of the invention or from the scope of the appended claims.

What is claimed is:

1. A pedicure tool comprises a generally ellipsoidal housing comprising a plurality of body panels, each one of the plurality of body panels having a periphery which mates with the corresponding periphery of the abutting body panel, each of the plurality of body panels having an opening extending therethrough, each of the openings releasably receiving a concave insert panel therein, each insert panel having an abrasive surface on the exterior thereof.

2. The pedicure tool of claim 1 comprising three body panels.

3. The pedicure tool of claim 2 wherein the three body panels are identical.

4. The pedicure tool of claim 1 wherein the body panels snap together.

5. The pedicure tool of claim 1 wherein each of the body panels forms a generally oval periphery which mates with the corresponding periphery of the abutting body panel.

6. The pedicure tool of claim 5 wherein snap elements along the peripheries of the body panels mate with corresponding snap elements on the other side of the body panels to releasably hold the body panels together.

7. The pedicure tool of claim 6 wherein the peripheries of the body panels are provided with interlocking teeth.

8. The pedicure tool of claim 1 wherein the abrasive surface is an abrasive grit.

9. The pedicure tool of claim 1 wherein the insert panels are retained within the openings by clips.

10. The pedicure tool of claim 1 further having a finger opening is provided along one side of each of the openings whereby a user engages the insert panel to easily remove same.

11. The pedicure tool of claim 1 further having a plurality of massager bumps are provided at one end of the housing.

12. The pedicure tool of claim 1 wherein two abutting insert panels are adapted to be removed whereby the portion of housing between the two removed insert panels forms a handle adapted to be grasped by a user.

13. A pedicure tool comprises a generally ellipsoidal housing comprised of three identical body panels, each of the body panels forming a generally oval periphery which mates with the corresponding periphery of the abutting body panel, the body panels having snap elements along the one side thereof which mate with corresponding snap elements on the other side of the body panels thereof to releasably hold the body panels together, each body panel having an opening extending therethrough, each of the three openings releasably receiving an insert panel therein, the insert panels being retained within the openings by clips, a finger opening being provided along one side of each of the openings whereby a user engages the insert panel to easily remove same, wherein two abutting insert panels are adapted to be removed whereby the portion of housing between the two removed insert panels forms a handle adapted to be grasped by a user, each insert panel having an abrasive grit on the exterior thereof.

14. The pedicure tool of claim 13 wherein the peripheries of the body panels are provided with interlocking teeth.

15. The pedicure tool of claim 13 further having a plurality of massager bumps are provided at one end of the housing.

\* \* \* \* \*